United States Patent [19]

Schmieding et al.

[11] Patent Number: 5,350,383
[45] Date of Patent: Sep. 27, 1994

[54] ADJUSTABLE DRILL GUIDE WITH INTERCHANGEABLE MARKING HOOKS

[75] Inventors: Reinhold Schmieding; Donald Grafton, both of Naples, Fla.

[73] Assignee: Arthrex, Inc., Naples, Fla.

[21] Appl. No.: 19,355

[22] Filed: Feb. 18, 1993

Related U.S. Application Data

[63] Continuation-in-part of Ser. No. 837,886, Feb. 20, 1992, Pat. No. 5,269,786.

[51] Int. Cl.$^5$ .............................................. A61F 5/04
[52] U.S. Cl. ........................................ 606/96; 606/103
[58] Field of Search .................... 606/96, 97, 98, 99, 606/100, 103, 88, 108

[56] References Cited

U.S. PATENT DOCUMENTS

| | | | |
|---|---|---|---|
| 4,672,957 | 6/1987 | Hourahane | 606/96 |
| 4,739,751 | 4/1988 | Sapega | 606/96 |
| 4,823,780 | 4/1989 | Odensten | 606/96 |
| 4,883,048 | 11/1989 | Purnell | 606/96 |
| 4,920,958 | 5/1990 | Walt | 606/103 |
| 5,112,337 | 5/1992 | Paulos | 606/96 |
| 5,163,940 | 11/1992 | Bourque | 606/96 |

FOREIGN PATENT DOCUMENTS

| | | | |
|---|---|---|---|
| 772536 | 10/1980 | U.S.S.R. | 606/96 |
| 876121 | 10/1981 | U.S.S.R. | 606/96 |

*Primary Examiner*—Robert A. Hafer
*Assistant Examiner*—David Kenealy
*Attorney, Agent, or Firm*—Ostrolenk, Faber, Gerb & Soffen

[57] ABSTRACT

An adjustable drill guide for marking a proper location of a bone tunnel for arthroscopic surgery. The drill guide includes an arc shaped outrigger, an adapter slidably coupled to the outrigger, a plurality of interchangeable marking hooks adapted to be received by said adapter, and a sighting device coupled to the outrigger. The sighting device is adapted to receive a guide pin for marking the tunnel position. One of the plurality of marking hooks is chosen and inserted into the adapter of the outrigger. The adapter is then slid along the outrigger to a marked position at which an angled tip of the marking hook becomes aligned with the sighting device. Next, the marking hook is inserted into the knee requiring surgery. The sighting device is then advanced towards the knee until it is directly adjacent the knee. A guide pin is inserted into the sighting device and drilled into the knee. The drill guide is removed, thereby leaving the guide pin in position for drilling the tunnel.

16 Claims, 5 Drawing Sheets

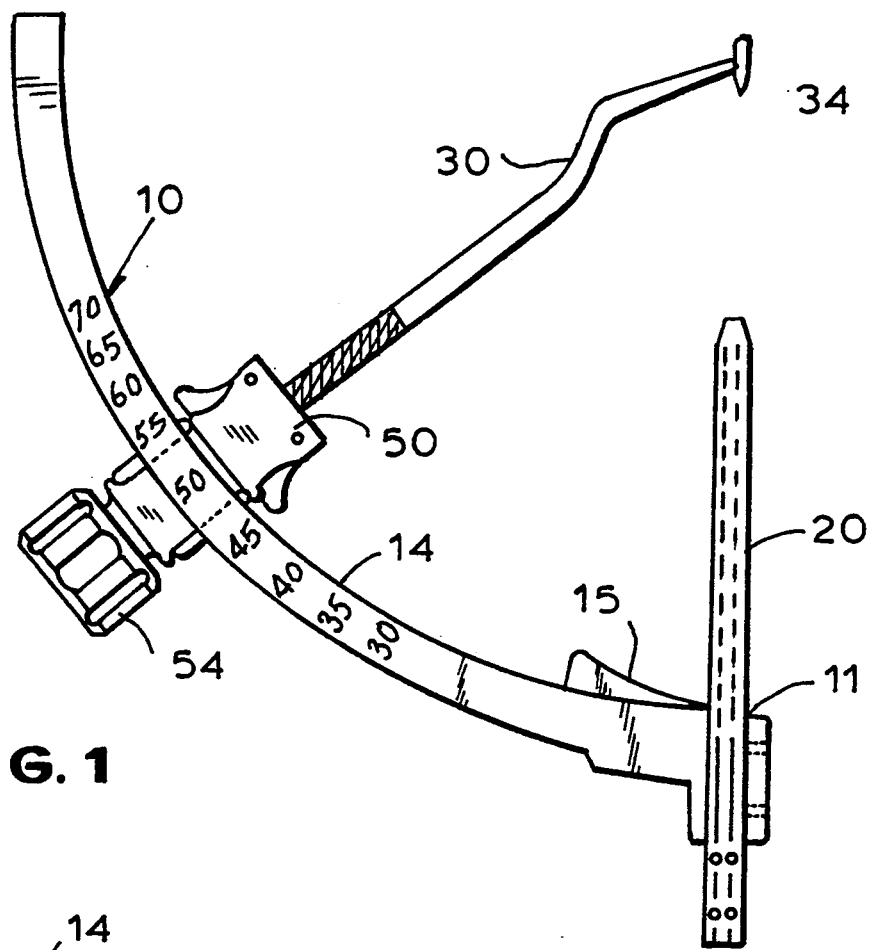
FIG.1
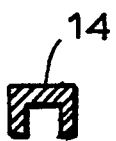
FIG.4
FIG.3
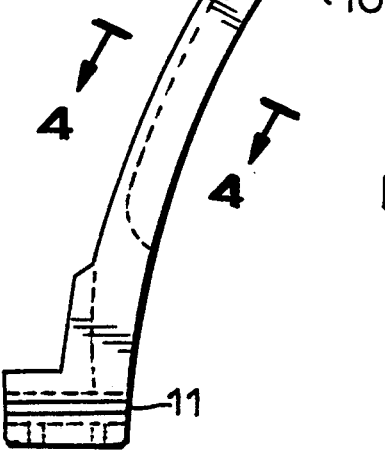
FIG.5
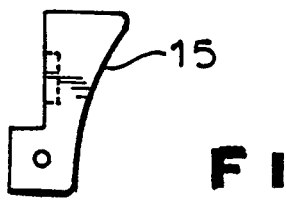
FIG.6
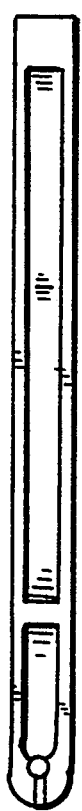

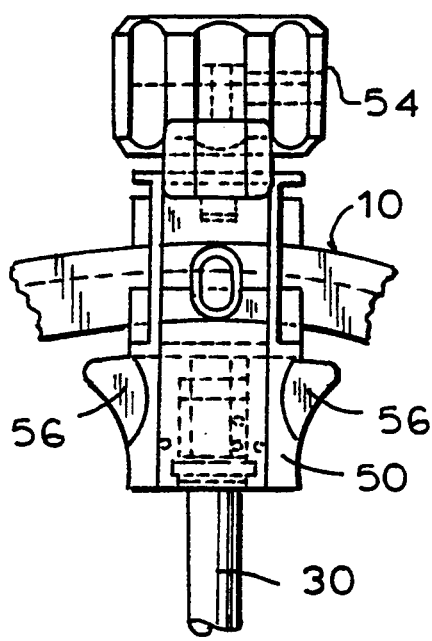
FIG.7
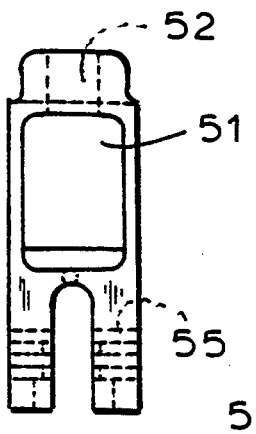
FIG.9
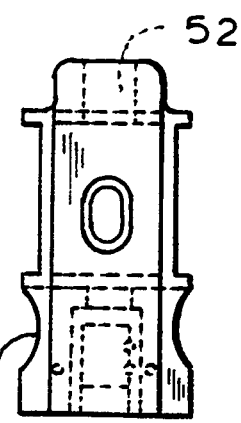
FIG.8
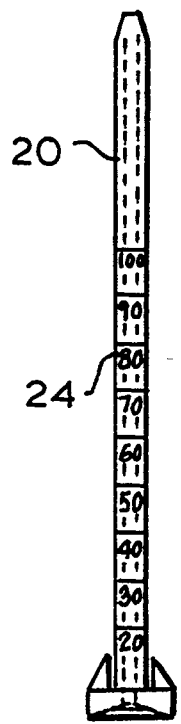
FIG.11
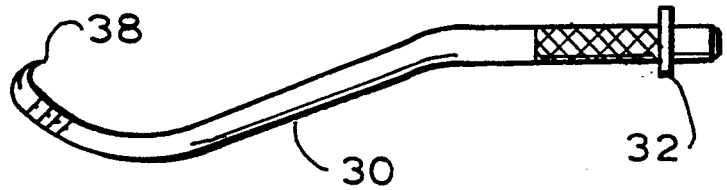
FIG.18A
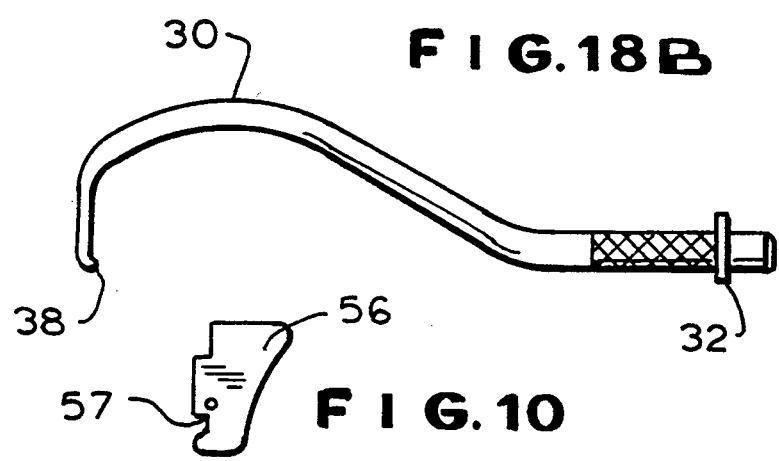
FIG.18B
FIG.10

ADJUSTABLE DRILL GUIDE WITH INTERCHANGEABLE MARKING HOOKS

This is a continuation-in-part of application Ser. No. 07/837,886, filed Feb. 20, 1992, now U.S. Pat. No. 5,269,786 the disclosure of which is herein incorporated by reference.

BACKGROUND OF THE INVENTION

1. Field of the Invention

The present invention relates to an adjustable drill guide for accurate tibial tunnel placement both inside and outside the knee in endoscopic ACL reconstruction and, more specifically, to a drill guide which can be used with a plurality of different marking hooks.

2. Description of the Related Art

In the past, the intra-articular entry point of the tibial tunnel has tended to be placed too far anterior, resulting in roof impingement and delayed graft failure. See, e.g., S. Howell, "A Rationale for Predicting ACL Graft Impingement by the Intercondylar Roof, A Magnetic Resonance Imaging Study", *Am. Jour. Sports Med.*, Vol. 19, No., pp. 276 (1991), herein incorporated by reference. This problem has occurred largely due to the absence of any constant bony landmarks in the intercondylar notch which can be used to orient placement of guide systems for accurate reproducible tibial tunnel guide pin placement.

Also, the tibial tunnel exit point outside the knee has tended to be placed too close to the joint line. This results in a short tibial tunnel such that the tibial bone plug of a completed bone patellar tendon bone autograft reconstruction resides outside the tibial tunnel and interference screw fixation cannot be used. A second problem caused by a high tibial tunnel exit point is that the angle of the tibial tunnel in reference to the joint line is too small, which will not allow transtibial tunnel instrumentation to reach the isometric area on the lateral femoral condyle to create a femoral socket for graft fixation.

SUMMARY OF THE INVENTION

The present invention overcomes the above-described problems in the prior art by utilizing the anatomic structure of the knee to consistently locate the ideal location of the tibial tunnel.

The one constant anatomic structure in the intercondylar notch of the anterior cruciate ligament (ACL) deficient knee is the posterior cruciate ligament (PCL). See, e.g., C. Morgan et al., "Arthroscopic Meniscus Repair Evaluated by Second Look Arthroscopy," *Am. Jour. Sports Med.*, Vol. 19, No. 6, p. 62 (1991), herein incorporated by reference. In the intact knee, there is an important anatomic interaction between the ACL and the PCL at their midpoints, whereby the intact ACL actually wraps around or bends over the PCL in terminal extension. This dynamic interaction is an integral part of the "screw home" mechanism of the knee. Ideally, during ACL reconstruction, the entry point in the knee for the tibial tunnel should be made far enough posterior to reconstruct this important relationship between the ACL graft and the intact PCL.

The proper entry point for tibial tunnel guide pin placement resides 7 mm anterior to the leading edge of the PCL at the level of the intercondylar floor. A 7 mm diameter graft placed through a 7 mm tibial tunnel centered at this point will: 1) reach an isometric femoral socket directly in line with the tibial tunnel with the knee in 70–80 degrees of flexion; 2) avoid roof impingement in full extension with a minimal notchplasty; and 3) reconstruct the "screw home" mechanism and the interaction between the ACL graft and the intact PCL.

The present invention consists of an adjustable arthroscopic drill guide which can be used with a variety of different marking hooks to position the sighting device at the proper entry angle. For example, the drill guide of the present invention can be used with marking hooks which reference the base portion of the PCL near its intercondylar floor from an anteromedial portal and automatically position an associated external sighting device so that it delivers a guide pin to an intra-articular entry point, 7 mm from the leading edge of the PCL at the intercondylar floor.

The marking tool and sighting device are positioned relative to each other by an arc shaped outrigger. The outrigger includes a slot along its length in which an adapter which holds the marking hook is slidably mounted and the sighting device is also adjustably mounted. The sighting device is adapted to receive a guide pin which marks the proper entry point into the knee for drilling of the tibial tunnel.

Each of the different marking hooks which can be used with the drill guide for ACL reconstruction includes a longitudinal tip which is aligned with the sighting device and thus indicates the angle at which the tunnel will be drilled. Preferably, separate tips are provided for tunnel angles of 50°, 60° and 70°. ACL tibial guide hooks, as well as PCL referenced hooks, can be used with the guide of the present invention. Moreover, new marking hooks can be added to the system as new procedures and corresponding marking hooks evolve. By choosing the appropriate marking hook, the guide can be converted between an ACL tibial guide and a PCL referenced guide. Thus, a surgeon need only purchase a single guide and adapter assembly.

The method of the present invention includes the steps of attaching the appropriate marking hook to the outrigger with an adapter, sliding the adapter along the slot of the outrigger to a predetermined position corresponding to the angle of the marking hook, locking the position of the adapter on the outrigger at that position, inserting the marking hook into the knee of a patient, advancing the sighting device towards the knee until it is directly adjacent the knee, inserting a guide pin into the sighting device, drilling the guide pin into the knee, and removing the apparatus, thereby leaving the guide pin in position for drilling the tibial tunnel.

With PCL referenced marking hooks, the guide pin is automatically positioned at an intra-articular entry point disposed 7 mm from the leading edge of the posterior cruciate ligament at the intercondylar floor.

Other features and advantages of the present invention will become apparent from the following description, when read in conjunction with the accompanying drawings.

BRIEF DESCRIPTION OF THE DRAWINGS

FIG. 1 shows the adjustable drill guide of the present invention.

FIG. 3 is a side view of the outrigger of the present invention.

FIG. 4 is a cross-section of the outrigger along line IV—IV of FIG. 3.

FIG. 5 is a side view of the trigger used to adjust the position of the sighting device.

FIG. 6 is a side view of the outrigger of FIG. 4.

FIG. 7 shows the adapter and nut assembly of the present invention.

FIG. 8 is a front view of the adapter.

FIG. 9 is a side view of the adapter.

FIG. 10 is a side view of the trigger of the adapter.

FIG. 11 shows the sighting device of the present invention.

FIGS. 18A and 18B show a PCL femoral and tibial marking hook.

DETAILED DESCRIPTION OF THE PREFERRED EMBODIMENT

Figure 2:
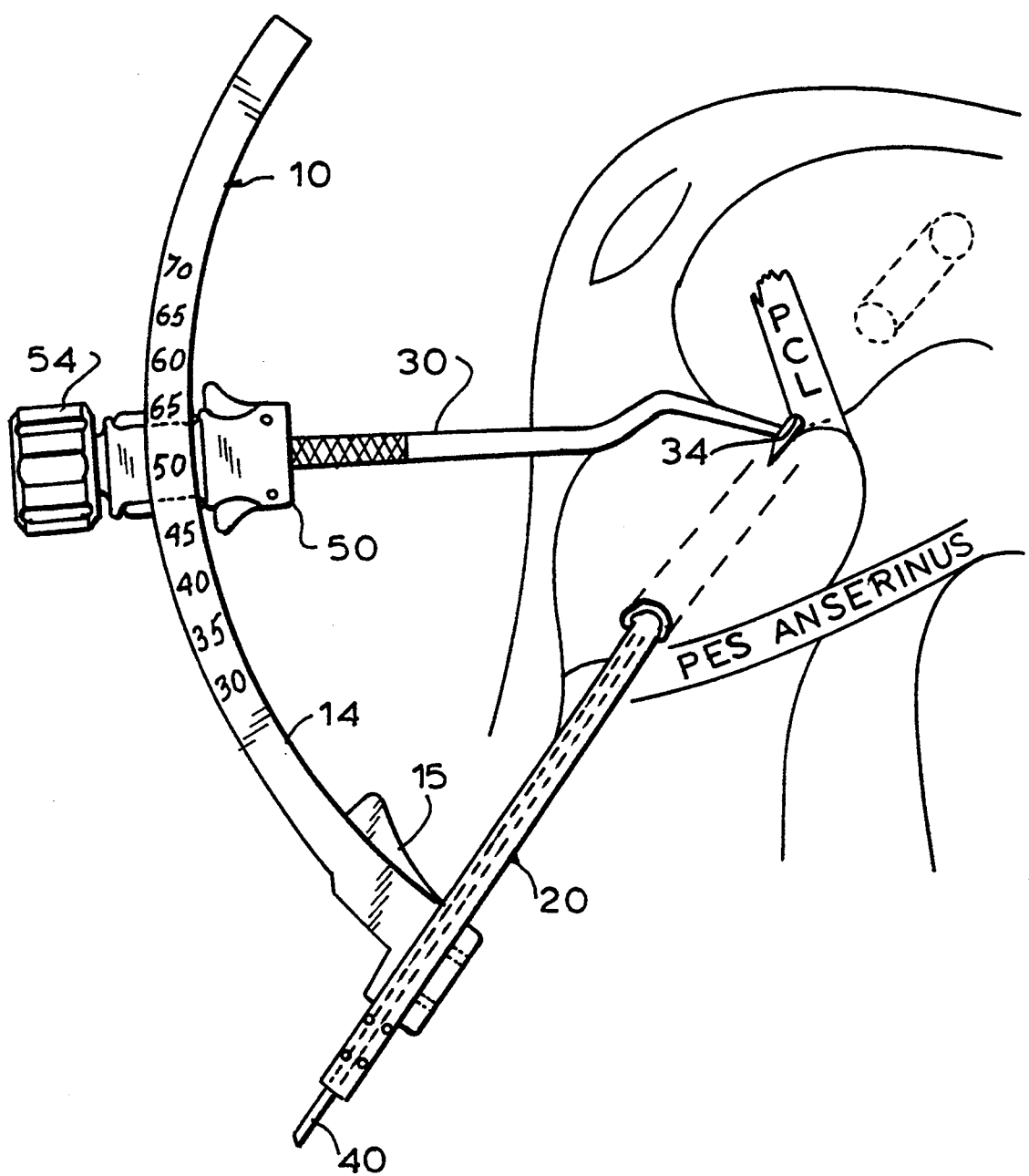
FIG. 2 shows the adjustable drill guide with the marking hook in place for locating the tibial tunnel.

Referring to FIG. 1, the present invention is an adjustable tibial drill guide consisting of an outrigger 10, an adjustable sighting device 20, an adapter 50 and an interchangeable marking hook 30. The outrigger 10 is arc shaped and includes a slot 14 along its length. The slot 14 slidably receives the adapter 50 holding marking hook 30.

The sighting device 20 is disposed at the bottom of the arc of outrigger 10, and receives a guide pin 40 which marks the proper location for the tibial tunnel. Sighting device 20 is arranged to be advanced towards the knee into engagement with the skin after it has been properly positioned. Due to the arcuate shape of outrigger 10 and the adjustability of the adapter and hook, sighting device 20 always locates the guide pin 40 so that it is aligned with, and at the same angle as, the angled tip of the marking hook. With PCL referenced hooks, the sighting device is located 7 mm anterior to the leading edge of the PCL at the intercondylar floor.

As shown in FIG. 1, sighting device 20 is slidably disposed through a bore 11 disposed at the lower end of outrigger 10. Spring loaded trigger release 15, shown in FIG. 5, is located adjacent bore 11. When trigger 15 is compressed, sighting device 20 is free to slide within bore 11.

As shown in FIG. 11, sighting device 20 includes etched markings 24 to measure the tunnel length before drilling to ensure sufficient tunnel length for interference screw fixation of the bone graft.

Referring now to FIGS. 7-10, the drill guide of 10 the present invention can be used with a plurality of different marking hooks, which will be discussed below. The adapter 50 includes a bore 52 through which the outrigger 10 extends. Bore 52 receives a screw-nut member 54. When screw-nut member 54 is loosened, adapter 50 is free to slide along slot 14. Adapter 50 receives the selected marking hook on the opposite side from screw-nut number 54; i.e., the marking hook is received on the inside of outrigger 10. Adapter 50 includes two spring loaded pivotable triggers 56 with respective jaws 57 at their inner surfaces. Each of the marking hooks shown in FIGS. 12A-18B includes a collar 32. The collared end of the hook is inserted into the adapter, such that jaws 57 engage the collar 32 of the hook. When the triggers are squeezed together, jaws 57 retract from collar 32, allowing the marking hook to be inserted or removed.

A plurality of different marking hooks are illustrated in FIGS. 12A-18B. The hooks shown in FIGS. 12A-17B each include a tip 4 which is angled with respect to the hook. Depending upon the desired angle of the tibial tunnel, a hook having a 50°, 60° or 70° angled tip can be used with the outrigger of the invention. As shown in FIG. 1, tip 34 and sighting device 20 are in perfect alignment. Thus, tip 34 shows the actual angle and path that the pin will follow when it is inserted into the knee. When exchanging marking hooks, the tip 34 and sighting device 20 are automatically aligned when the adapter is slid along outrigger 10 to the specified position for that marking hook (e.g. 50° in FIG. 1). Each of the hooks includes knurled area 33 for grasping the hook when inserting the same into the adapter.

Figure 12A:
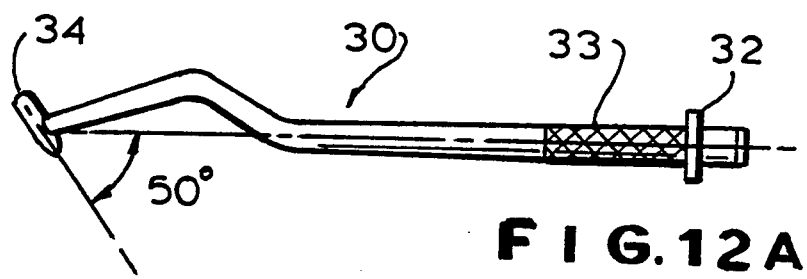
FIGS. 12A and 12B illustrate a 50° angled tibial marking hook.
Figure 12B:
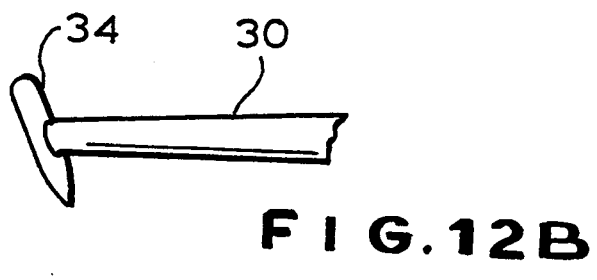
Figure 13A:
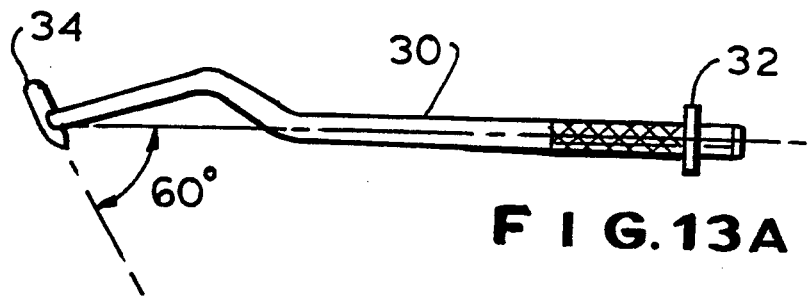
FIGS. 13A and 13B show a 60° angled tibial hook.
Figure 13B:
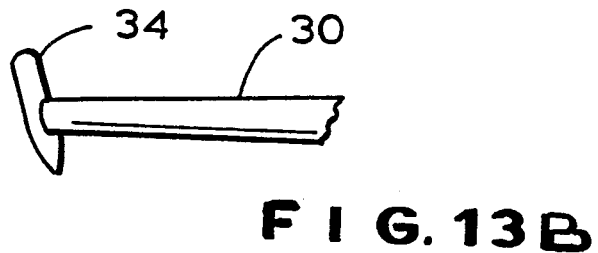
Figure 14A:
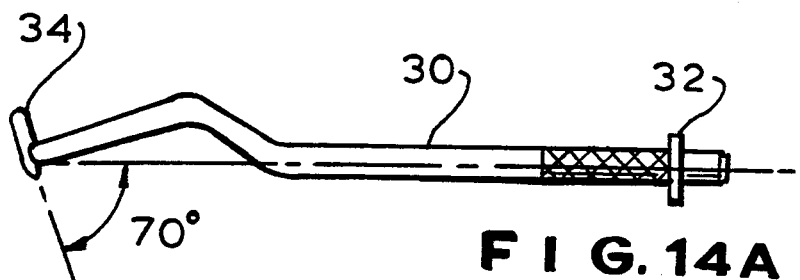
FIGS. 14A and 14B show a 70° angled tibial hook.
Figure 14B:
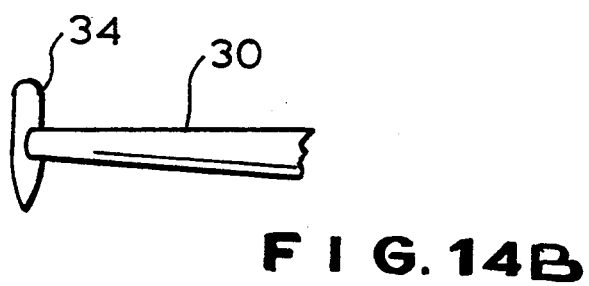

FIGS. 12A and 12B show a 50° oriented tibial marking hook. In FIGS. 13A and 13B, tip 4 is oriented at an angle of 60° and in FIGS. 14A and 14B, the tip has an angle of 70°.

Figure 15A:
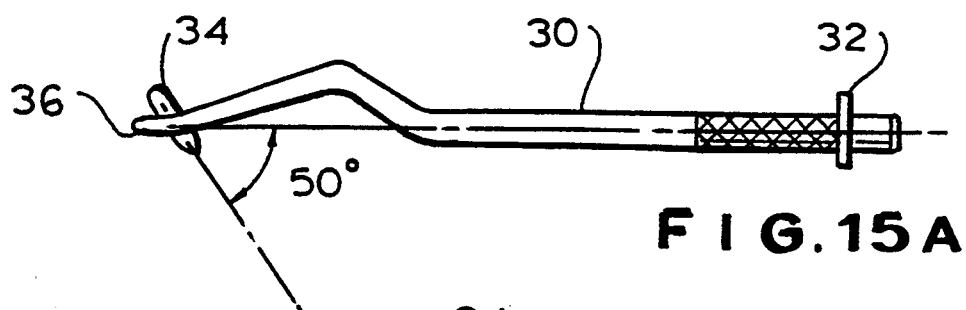
FIGS. 15A and 15B show a 50° angled tibial hook having a PCL reference.
Figure 15B:
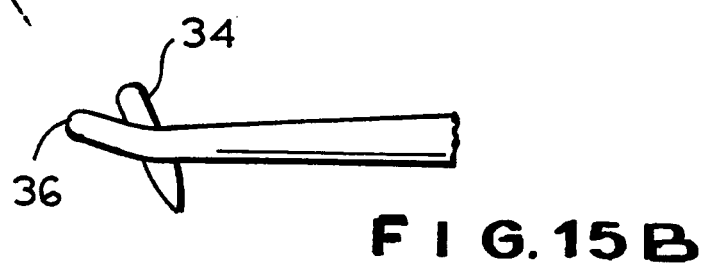
Figure 16A:
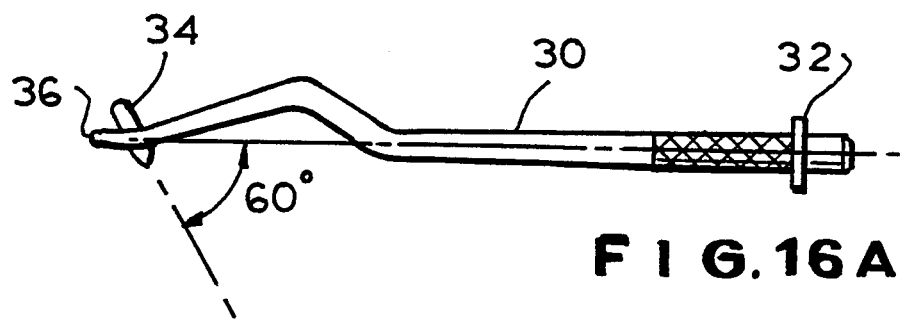
FIGS. 16A and 16B show a 60° angled tibial hook having a PCL reference.
Figure 16B:
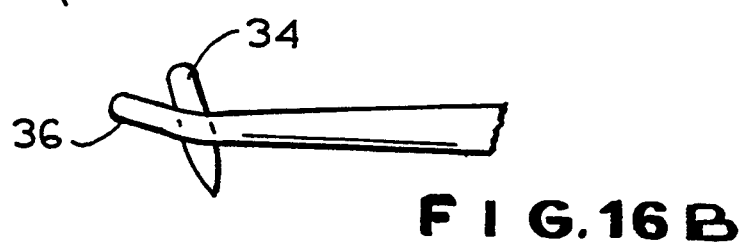
Figure 17A:
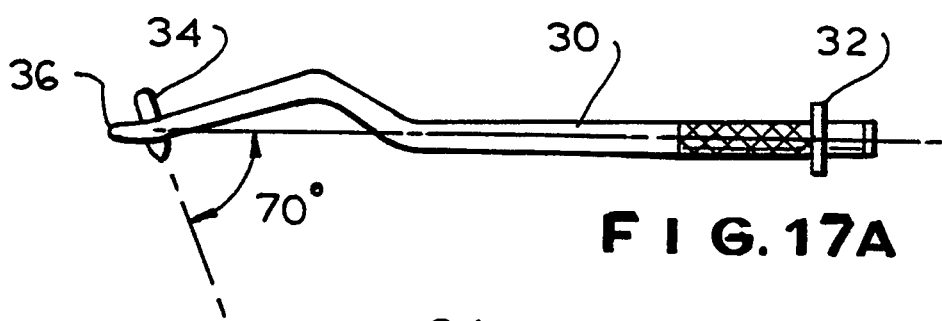
FIGS. 17A and 17B illustrate a 70° angled tibial hook having a PCL reference.
Figure 17B:
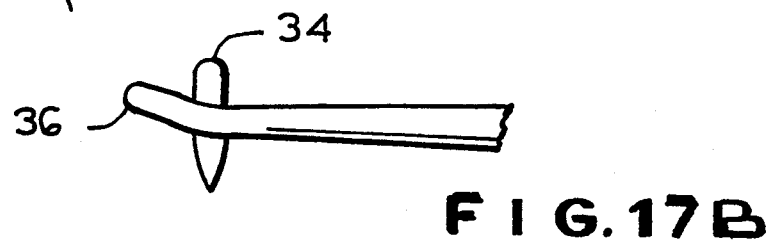

FIGS. 15A-17B show the marking hooks with an extension 36 for referencing the PCL. When the hook is inserted into the knee, extension 36 abuts against the base of the PCL. The tip of FIGS. 15A and 15B is angled 50° from the hook. In FIGS. 16A, 16B and 17A, 17B, the tip is angled at 60° and 70° respectively FIG. 18A illustrates a PCL femoral marking hook which can be used to orient the sighting device by inserting the hook through the femur. The hook end 38 grasps the PCL. FIG. 18B shows a tibial PCL marking hook.

The method of the invention will now be described in conjunction with FIGS. 1 and 2. First, the appropriate marking hook 30 is chosen and inserted into adapter 50 of outrigger 10. Adapter 50 is then slid along the outrigger (via slot 14) to the appropriate position corresponding to the angle of the chosen marking hook 30. The adapter 50 is then locked in this position on the outrigger 10 by tightening screw member 54, and the marking hook is inserted into the patient's knee. (This step of the procedure can be reversed; i.e., the adapter can be inserted into the knee before adjustment and locking on the outrigger.) Next, the sighting device 20 is advanced towards the knee to a position directly adjacent the skin by activating trigger 15. Guide pin 40 is then inserted into the sighting device and drilled 10 into the knee. The guide is then removed, leaving the guide pin 40 in position so that a cannulated drill may be placed over the guide pin 40 for drilling the tibial tunnel.

The drill guide of the present invention provides a device for arthroscopic surgery which, for the first time, provides an indication to the surgeon of the exact path and angle of the tibial tunnel to be drilled. Moreover, the drill guides with the PCL extension advantageously utilizes the only constant structure in the knee, i.e. the relationship between the PCL and the ACL, to position the guide pin such that the intra-articular guide pin entry point will always be 7 mm anterior to the leading edge of the PCL. The resultant tibial tunnel is also properly angled for drilling a femoral tunnel directly in line with the tibial tunnel.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An adjustable drill guide for arthroscopic anterior cruciate ligament surgery, comprising:
    an outrigger in the shape of an arc of a circle having a center;
    a sighting device coupled to said outrigger, said sighting device having a longitudinal axis extending toward said center of said circle, said sighting device being adapted to receive a guide pin for marking a position for drilling a tibal tunnel;
    a plurality of different selectable interchangeable marking hooks, each selected one of said plurality of interchangeable marking hooks having a proximal end, a distal end, and a central axis extending from said proximal end to said distal end, said proximal end being mountable on said outrigger such that central axis of said selected marking hook is disposed at a selected predetermined angle with respect to said longitudinal axis of said sighting device, said selected predetermined angle corresponding to said selected marking hook;
    a tip located at said distal end of each of said marking hooks, said tip comprising a straight longitudinal member extending through said distal end, said tip having opposed ends projecting from opposite sides of said distal end, a first of said opposed ends extending toward said sighting device and a second of said opposed ends extending away from said sighting device, said tip being oriented at said selected predetermined angle with respect to said central axis of said marking hook; and
    means slidably coupled to said outrigger for receiving one of said plurality of different interchangeable marking hooks, said means for receiving one of said interchangeable marking hooks being slidable along said outrigger to a marked position corresponding with said selected predetermined angle, whereby said tip is automatically aligned with said guide pin so as to provide a visual indication of guide pin position and angle.

2. The drill guide of claim 1, wherein said means slidably coupled to said outrigger comprises an adapter.

3. The drill guide of claim 2, wherein said outrigger has a longitudinal arcuate slot and said adapter is slidably secured in said slot.

4. The drill guide of claim 3, wherein said adapter is slidably secured in said slot of said outrigger by a screw-nut member, said screw-nut member being removably received in said adapter, wherein when said screw-nut member is loosened said adapter is free to slide in said slot.

5. A method of marking a proper location of a tibial tunnel for arthroscopic anterior cruciate ligament reconstruction using an adjustable drill guide, said drill guide comprising an outrigger in the shape of an arc of a circle having a center, an adapter slidably coupled to said outrigger, a sighting device coupled to said outrigger, said sighting device having a longitudinal axis extending toward said center of said circle, said sighting device being adapted to receive a guide pin for marking said tibial tunnel position, and a plurality of different selectable interchangeable marking hooks, each of said plurality of marking hooks having a proximal end, distal end, and a central axis extending from said proximal end to said distal end, said proximal end being mountable on said outrigger such that said central axis of said selected marking hook is disposed at a selected predetermined angle with respect to said longitudinal axis of said sighting device, said selected predetermined angle corresponding to said selected marking hook, said method comprising the steps of:
    inserting one of said plurality of interchangeable marking hooks into said adapter, each of said interchangeable marking hooks having a tip located at said distal end, said tip comprising a straight longitudinal member extending through said distal end, said tip having opposed ends projecting from opposite sides of said distal end, a first of said opposed ends extending toward said sighting device and a second of said opposed ends extending away from said sighting device, said tip being oriented at said selected predetermined angle with respect to said central axis of said marking hook;
    sliding said adapter along said outrigger to a marked position on said adapter corresponding with said selected predetermined angle;
    inserting said marking hook into a knee requiring anterior cruciate ligament reconstruction;
    advancing said sighting device towards the knee until it is directly adjacent the knee;
    inserting a guide pin into said sighting device, said guide pin being automatically aligned with said tip;
    drilling said guide pin into the knee; and
    removing the tibial guide, thereby leaving said guide pin in position for drilling a tibial tunnel.

6. The drill guide of claim 1, wherein said predetermined angle is 50°.

7. The drill guide of claim 1, wherein said selected predetermined angle is 60°.

8. The drill guide of claim 1, wherein said selected predetermined angle is 70°.

9. The drill guide of claim 1, further comprising an extension disposed at said distal end for abutting against a base of a posterior cruciate ligament and positioning said tip at a predetermined distance from a leading edge of said posterior cruciate ligament.

10. The drill guide of claim 9, wherein said selected predetermined angle is 50°.

11. The drill guide of claim 9, wherein said selected predetermined angle is 60°.

12. The drill guide of claim 9, wherein said selected predetermined angle is 70°.

13. The drill guide of claim 1, wherein said means for receiving includes spring-loaded grasping means for releasably grasping one of said plurality of interchangeable marking hooks.

14. The drill guide of claim 13, wherein said grasping means comprises a pair of spring-loaded triggers pivotally disposed within said adapter, wherein when said triggers are compressed one of said plurality of interchangeable marking hooks can be inserted or removed from said adapter.

15. The drill guide of claim 14, wherein each of said triggers includes a jaw, each of said plurality of interchangeable marking hooks including a collar disposed on a proximal end, wherein when one of said plurality of interchangeable marking hooks is inserted into said adapter each said jaw grasps the collar to secure said interchangeable marking hook within said adapter.

16. A tibial tunnel guide for accurately locating a position for a tibial tunnel for arthroscopic anterior cruciate ligament reconstruction by referencing a base of a posterior cruciate ligament at an intercondylar floor, said tibial tunnel guide comprising:

an outrigger in the shape of an arc of a circle having a center;

a sighting device coupled to said outrigger, said sighting device having a longitudinal axis extending toward said center of said circle, said sighting device being adapted to receive a guide pin for marking a position for drilling a tibial tunnel;

a plurality of different selectable interchangeable marking hooks, each selected one of said plurality of interchangeable marking hooks having a proximal end, a distal end and a central axis extending from said proximal end to said distal end, said proximal end being mountable on said outrigger such that said central axis of said selected marking hook is disposed at a selected predetermined angle with respect to said longitudinal axis of said sighting device, said selected predetermined angle corresponding to said selected marking hook, a tip located at said distal end, said tip comprising a straight longitudinal member extending through said distal end, and an extension disposed at said distal end and extending from said tip for abutting against the base of the posterior cruciate ligament and positioning said tip at a predetermined distance from a leading edge of the posterior cruciate ligament at the intercondylar floor; and means coupled to said outrigger for receiving one of said plurality of selectable interchangeable marking hooks, said means for receiving one of said interchangeable marking hooks being slidable along said outrigger to a marked position corresponding with said selected predetermined angle;

wherein, when said means for receiving one of said interchangeable marking hooks is slid along said outrigger to said marked position corresponding with said predetermined angle and when said extension disposed at the distal end of said interchangeable marking hook is positioned at the base of said posterior cruciate ligament, said sighting device is automatically positioned so as to direct said guide pin to an intra-articular entry point disposed at said predetermined distance from the leading edge of the posterior cruciate ligament at the intercondylar floor.

* * * * *

UNITED STATES PATENT AND TRADEMARK OFFICE
CERTIFICATE OF CORRECTION

PATENT NO. : 5,350,383
DATED : September 27, 1994
INVENTOR(S) : Reinhold Schmieding, Donald Grafton and Craig D. Morgan It is certified that error appears in the above-indentified patent and that said Letters Patent is hereby corrected as shown below:

On the title page, item [75]: Inventors, add --Craig D. Morgan, Greenville, Dela.--.

Signed and Sealed this

Thirteenth Day of December, 1994

Attest:

BRUCE LEHMAN

Attesting Officer          Commissioner of Patents and Trademarks